Oct. 22, 1963 LU VERNE P. GOLIE Plant Pat. 2,291
CLIMBING ROSE PLANT
Filed May 31, 1962 2 Sheets-Sheet 1
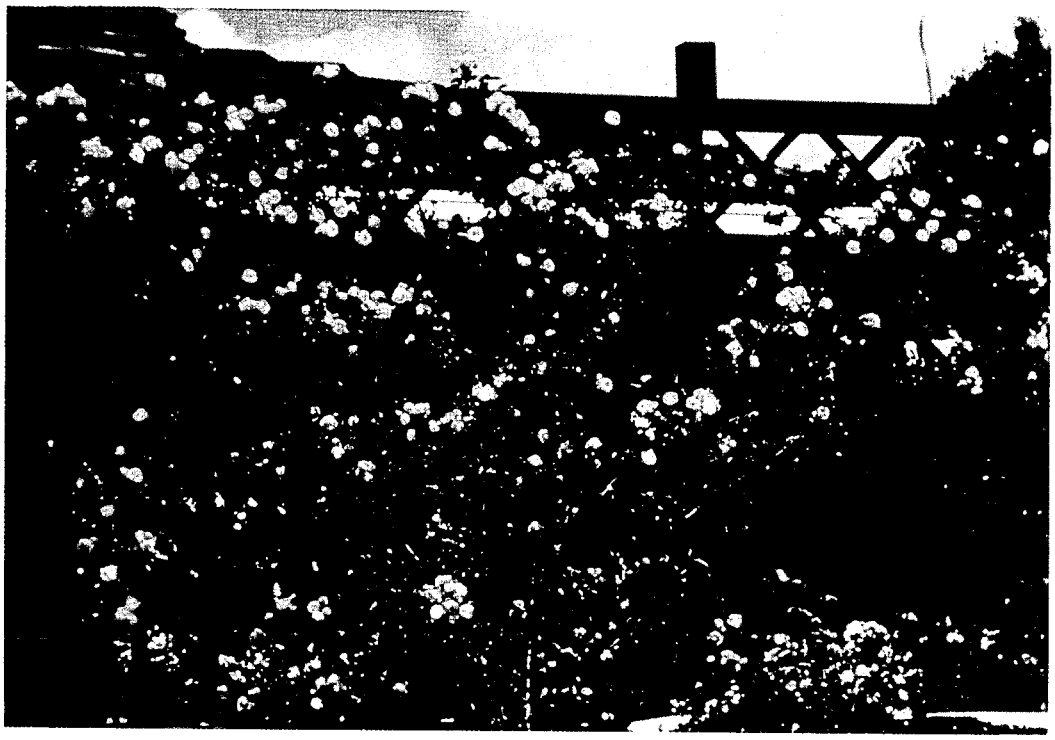
INVENTOR:
LU VERNE P. GOLIE
BY Rummler & Snow
ATT'YS

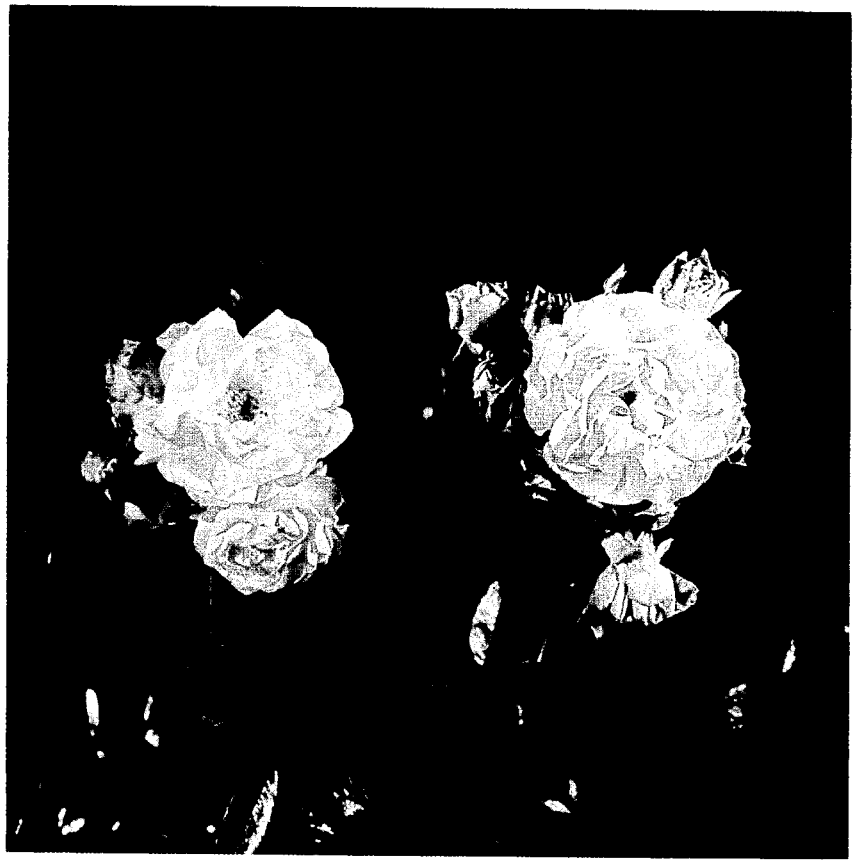
INVENTOR:
LuVERNE P. GOLIE
BY: Rummler & Snow
ATT'YS

United States Patent Office

Plant Pat. 2,291
Patented Oct. 22, 1963

2,291
CLIMBING ROSE PLANT

Lu Verne P. Golie, 34595 Alvarado-Niles Road, Union City, Calif.

Filed May 31, 1962, Ser. No. 199,207
1 Claim. (Cl. Plt.—5)

This disclosure concerns my discovery of a new and distinct variety of climbing rose plant. This new variety originated as a sport of the well known "Margo Koster" rose bush (unpatented) and was discovered by me in my nursery at San Leandro, California, during the work of cultivating and propagating the parent plant.

This new sport was observed to have definite climbing characteristics, not possessed by the original plant, and when planted in my garden for trial the new plant was found to have, in addition to its strong climbing habit, a vigorous habit of spreading growth, and a tendency to produce larger flowers than the bush-type "Margo Koster." It was also found that the flowers of the new variety tend to be more brilliant and to have almost double the number of petals than the flowers of "Margo Koster." This combination of features serves to provide an unusually attractive climbing rose plant.

My new variety of climbing rose has been asexually reproduced by buds at nursery grounds in Livermore, California, and successive propagations have demonstrated that its novel characteristics are fixed and hold true from generation to generation. Propagation of the new variety is presently being carried on by budding at Livermore, California.

The accompanying drawings, Sheet 1 is a photograph showing my new variety of climbing rose plant and illustrating its vigorous climbing and spreading growth habit and Sheet 2 is a photograph showing a comparison of the blossoms of the new variety, on the right, with the parent "Margo Koster" on the left. A detailed description of the new variety is as follows, the color designations being according to the British Colour Council Horticultural Colour Chart.

*The Plant*

Origin: Sport of "Margo Koster" (unpatented).
Classification: Climbing rose.
Form: Climber.
Height: 8 feet—in one year of growth.
Spread: 10–12 feet—in one year of growth.
Branching: Espalier type of branching canes, willowy and easily trained against wall or fence.
Growth: Very vigorous.
Strength: Sturdy, but pliable.
Leaves:
*Quantity.*—Abundant.
*Size of leaf.*—4¼ to 4½ inch x 8 to 8½ inches. Leaflets.—Size, ¾ to ⅞ inch wide x 2¼ to 2½ inches long; number—7, occasionally 9. Note: on side branch appearing later in the year, after the first spring flush of heavy cane, the leaves are much smaller, the leaves being 2¼ to 2½ inches x 3½ to 3¾ inches and the leaflets being ⅜ to ½ inch wide x 1 to 1½ inches long.
*Shape.*—Long—with much space between leaflets. Leaflet margins undulated.
*Texture.*—Smooth, rather thin leathery, and very glossy.
*Color.*—Upper side, Spinach Green (0960/1). Under side, Spinach Green (0960/3).
*Petioles.*—1/16 inch long; 3/16 to ⅜ inch long on terminal leaflet.
*Ribs and veins.*—Not at all prominent.
*Rachis.*—Grooved on upper surface and having 8 to 10 small prickles on lower surface.
Thorns: The plant has relatively few thorns.

*Size.*—⅛ x 5/16 inch at base, ⅜ inch high, and downwardly curved.
*Color.*—Citron Green (763).

*Flower Bud*

Form: Globular—almost spherical.
Size: Averages slightly larger than "Margo Koster."
*Diameter.*—½ to ⅝ inch.
*Depth.*—⅝ to ¾ inch.
Opens slowly.
Color: Rose Pink (420/1) when sepals first divide. Rose Pink (420/1) tinged with light scarlet at margins of outer side of petals, when petals begin to unfurl.
Sepals: Spear shaped; curl back very early during bud opening period and when bud is very small. Color—inside—Willow Green (000862/1); outside—Fern Green (0862).
Calyx: Funnel shaped.
*Size.*—Small; each calyx lobe or sepal ⅛ inch wide and ¼ to ⅝ inch long.
*Aspect.*—Hairy—fine pubescence. Not glandular.
Peduncle: 3/16 inch wide x 3/16 to ¼ inch long when flower is fully opened. Hairy aspect, with fine pubescence. Color—Scheeles Green (860/1).

*Flower*

Blooming period: Continuously from early spring through late fall. Blooms profusely during spring, moderately in midseason, and abundantly throughout fall.
Size of bloom: Medium.
*Diameter.*—1½–1¾ inches.
*Depth.*—¾ inch.
Borne: In clusters—3 to 25 blooms per cluster.
Shape: Rounded center when bloom first opens. Shape changes, as bloom matures, tends to become regularly imbricate.
Petalage:
*Number of petals.*—30 to 42.
*Arrangement.*—Regularly imbricate—occasionally irregularly imbricate.
*Form.*—Obovate.
*Color of petals.*—Upper side—Porcelain Rose (620). Upper side—at base—½ inch arc of white. Reverse side—Porcelain Rose (620/1–620/2).
Petals stay on stem for 10 days to 2 weeks in spring and then drop cleanly.
Petaloids:
*Number.*—5 to 6.
*Size.*—Small, often curl up.
*Color.*—Same as petals.
Peduncle:
*Length.*—1–1¼ inches.
*Stem of flower cluster.*—3½ to 9½ inches long, slender and upright.
*Color.*—Scheeles Green (860/1).
Discoloration after bloom: Darkens to Scarlet (19/1) with base portion remaining white.
Texture: Soft. Appearance—velvety.
Effect of weather: Flowers lightened by hot weather and open poorly in very wet cold weather.
Persistence: Flower finally drops off clean.
Fragrance: None.
Lasting quality:
*On plant.*—10 days to 2 weeks in spring; 5 to 7 days during summer at temperatures up to 95° F.
*As cut flower.*—7 to 9 days at room temperature.

*Genital Organs*

Stamens:
*Anthers.*—Regularly arranged, 1/16 inch long, and 50 to 60 in number.
*Pollen.*—Color—Indian Yellow (6/2).

*Filaments.*—⅛ to ¼ inch long. Color—Indian Yellow (6).

Pistils: ¼ inch long; 25 to 30 in number.

*Stigmas.*—Color—Uranium Green (63/1).

*Seeds.*—Sterile, very closely packed and covered with silver pubescence.

From the foregoing description it will be seen that my new plant discovery is in detail very similar to its parent, the well known "Margo Koster" bush type rose plant, the new variety being particularly distinguished from its parent by its vigorous spreading and climbing habit of growth. In addition the new variety is distinguished from "Margo Koster" by its somewhat larger flowers which have from 30 to 42 petals as compared with the 14 to 30 petals in the flowers of "Margo Koster."

Also, in "Margo Koster," almost one-half of each flower petal is white whereas in the new climbing variety each petal has only an arc of white at its base. In other details the new variety appears to be substantially identical with its parent.

Having thus disclosed my discovery of a new climbing rose plant, I claim:

A new and distinct variety of climbing rose plant, substantially as shown and described, characterized by its similarity to the bush type "Margo Koster" and distinguished by its vigorous climbing and spreading habit of growth, its espalier type of branching with willowy easily trained canes, and by its flowers which are somewhat larger and more brilliant in color than those of "Margo Koster."

No references cited.